(12) United States Patent
Rabbani et al.

(10) Patent No.: US 8,394,949 B2
(45) Date of Patent: *Mar. 12, 2013

(54) MULTISIGNAL LABELING REAGENTS, AND PROCESSES AND USES THEREFOR

(75) Inventors: Elazar Rabbani, New York, NY (US); Jannis G. Stavrianopoulos, Bayshore, NY (US); James J. Donegan, Long Beach, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/399,393

(22) Filed: Mar. 6, 2009

(65) Prior Publication Data

US 2009/0258374 A1    Oct. 15, 2009

Related U.S. Application Data

(62) Division of application No. 10/407,818, filed on Apr. 3, 2003, now Pat. No. 7,514,551.

(51) Int. Cl.
| | |
|---|---|
| C07H 19/04 | (2006.01) |
| C07H 7/06 | (2006.01) |
| C07H 5/04 | (2006.01) |
| C07H 1/00 | (2006.01) |
| C12Q 1/68 | (2006.01) |
| C12P 19/34 | (2006.01) |

(52) U.S. Cl. ............. 536/26.6; 536/22.1; 536/29.2; 536/55.1; 536/123.1; 435/6.1; 435/91.1

(58) Field of Classification Search ............. 536/22.1, 536/26.6, 29.2, 55.1, 123.1; 435/6, 91.1
See application file for complete search history.

(56) References Cited

U.S. PATENT DOCUMENTS

| | | | |
|---|---|---|---|
| 4,257,774 A | 3/1981 | Richardson et al. | |
| 4,547,569 A | 10/1985 | Letsinger et al. | |
| 4,692,509 A | 9/1987 | Dattagupta | |
| 4,948,882 A | 8/1990 | Ruth | |
| 4,996,143 A | 2/1991 | Heller | |
| 5,175,270 A | 12/1992 | Nilsen et al. | |
| 6,046,038 A * | 4/2000 | Nilsen | 435/91.1 |
| 7,166,478 B2 | 1/2007 | Stavrianopoulos et al. | |
| 2004/0161741 A1 | 8/2004 | Rabbani et al. | |
| 2005/0137388 A1 | 6/2005 | Rabbani et al. | |
| 2006/0024738 A1 | 2/2006 | Rabbani et al. | |
| 2010/0273145 A1 | 10/2010 | Pergolizzi et al. | |

FOREIGN PATENT DOCUMENTS

| | | |
|---|---|---|
| EP | 0450594 | 10/1991 |
| WO | WO 00/29624 | 5/2000 |
| WO | WO 01/72766 | 10/2001 |

OTHER PUBLICATIONS

Asseline et al., Oligodeoxynucleotides covalently linked to intercalating dyes as base sequence-specific ligands. influence of dye attachment site, EMBO , 1984, 795-800, 3.

Canellakis et al., Diacridines-double intercalators as chemotherapeutic agents, Biochemical Pharmacology, 1976, 231-236, 25.

(Continued)

*Primary Examiner* — Jezia Riley

(74) *Attorney, Agent, or Firm* — Elie Gendloff, Esq.

(57) ABSTRACT

The present invention provides multisignal labeling reagents and these are useful in a number of biochemical applications, including the manufacture of biomolecular probes and their use in detecting or amplifying analyte-specific moieties.

14 Claims, 1 Drawing Sheet

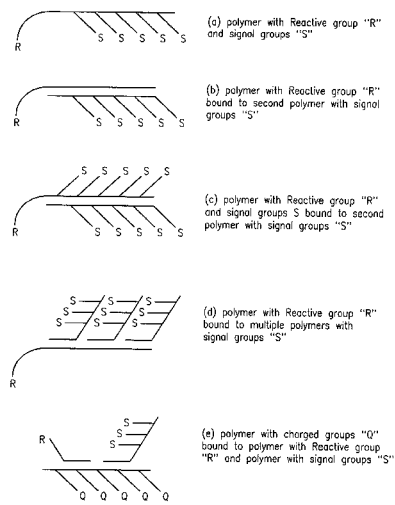

Examples of arrangements of R, S and Q in polymers

OTHER PUBLICATIONS

Canellakis et al., Diacridines:bifunctional intercalators I. chemistry, physical chemistry and growth inhibitory properties, Biochimica et Biophysica Acta,1976, 277-289, 418.

Canellakis et al., Diacridines:bifunctional intercalators II. The biological effects of putrescine, spermidine and spermine diacridines on HeLa cells and on the L-1210 and P-388 leukemia cells, Biochimica et Biophysica Acta,1976, 290-299, 418.

Canellakis et al., Diacridines:bifunctional intercalators III. definition of the general site of action, Biochimica et Biophysica Acta,1976, 300-314, 418.

Capelle et al., Deoxyribonucleic acid bifunctional intercalators: kinetic investigation of the binding of several acridine dimers to deoxyribonucleic acid, Biochemistry, 1979, 3354-3362, 18.

Chen et al., Diacridines, bifunctional intercalators. chemistry and antitumor activity, Journal of Medicinal Chemistry, 1978, 868-874, 21.

Christy et al., DNA binding site of the growth factor-inducible protein Zif268, PNAS, 1989, 8737-8741, 86.

Elling et al., Conversion of antagonist-binding site to metal ion site in the tachykinin NK-1 receptor, Nature, 1995, 74-77, 374.

Fico et al., Bifunctional intercalators: relationship of antitumor activity of disacridines to the cell membrane, Science, 1977, 53-56, 198.

Gaugain et al., DNA bifunctional intercalators. 1. Synthesis and conformational properties of an ethidium homodimer and of an acridine ethidium heterdimer, Biochemistry, 1978, 5071-5077, 17.

Gaugain et al., DNA bifunctional intercalators. 2. Florescence properties and Dna binding interaction of an ethidium homodimer and an acridine ethidium heterodimer, Biochemistry, 1978, 5078-5088, 17.

Genest et al., Investigation of DNA dynamics and drug-DNA interaction by steady state fluorescence anistropy, Nucleic Acids Res., 1985, 2603-2615, 13.

Georghiou, S., Interaction of acridine drugs with DNA and nucleotides, Photochemistry and Photobiology, 1977, 59-68, 26.

Glover et al., Hairpin-shaped heterometallic luminescent lanthanide complexes for DNA intercalative recognition, J. Am. Chem. Soc., 2003, 9918-9919, 125.

Hampshire, A. and Fox, K., Preferred binding sites for the bifunctional intercalator TANDEM determined using DNA fragments that contain every symmetrical hexanucleotide sequence, Analytical Biochemistry, 2008, 298-303, 374.

Hannon, M., Supramolcular DNA recognition, Chemical Society Reviews, 2007, 280-295, 36.

King et al.: Interactions of some novel amide-linked Bis(acridines) with deoxyribonucleic acid, Biochemistry, 1982, 4982-4989, 21.

Kobuta, Y. and Steiner, R., Fluorescence decay and quantum yield characteristics of acridine orange and proflavine bound to DNA, Biophysical Chemistry, 1977, 279-289, 6.

Loakes, D., The applications of universal DNA base analogues, Nucleic acids Res. 2001, 2437-2447, 29.

Mincheva et al., Chromosomal integration sites of human papillomavirus dna in three cervical cancer cell lines mapped by in situ hybridization, Med Microbiol Immunol.,1987, 245-256, 176.

Maloney et al., Synthesis of acridine-based DNA bis-intercalating agents, Molecules, 2001, 230-243, 6.

Timtcheva et al., Homodimeric monomethine cyanine dyes as fluorescent probes of biopolymers, J. Photochemistry and Photobiology B: Biology, 2000, 130-135, 58.

Wakelin et al., Structural limitations on the bifunctional intercalation of diacridines into DNA, Biochemistry, 1978, 5057-5063, 17.

Wright et al., Effects of ring substituents and linker chains on the bifunctional intercalation of diacridines into deoxyribonucleic acid, Biochemistry, 1980, 5825-5836, 19.

\* cited by examiner

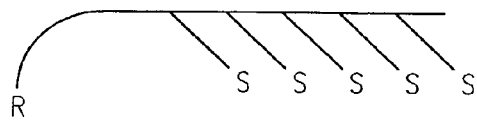
(a) polymer with Reactive group "R" and signal groups "S"

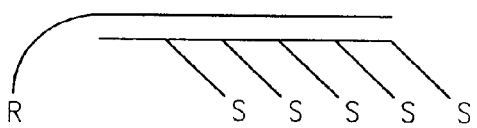
(b) polymer with Reactive group "R" bound to second polymer with signal groups "S"

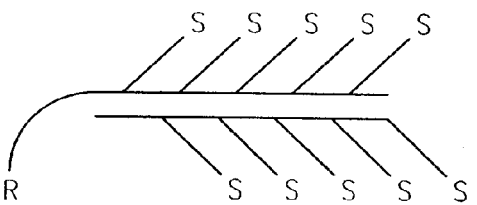
(c) polymer with Reactive group "R" and signal groups S bound to second polymer with signal groups "S"

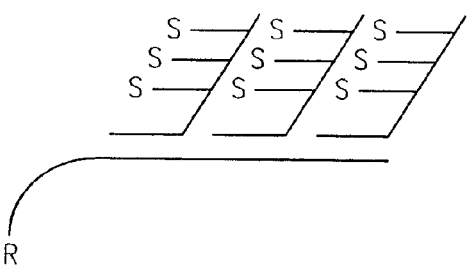
(d) polymer with Reactive group "R" bound to multiple polymers with signal groups "S"

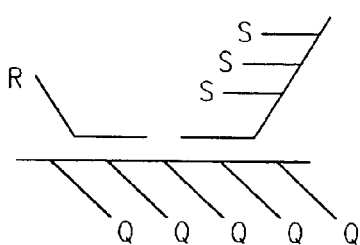
(e) polymer with charged groups "Q" bound to polymer with Reactive group "R" and polymer with signal groups "S"

Examples of arrangements of R, S and Q in polymers

SEQUENCE LISTING

```
<160> NUMBER OF SEQ ID NOS: 16

<210> SEQ ID NO 1
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1 ttuttttut ttttuttttt uttttutttt ttu                              33

<210> SEQ ID NO 2
<211> LENGTH: 29
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<223> OTHER INFORMATION: 3'-amidated

<400> SEQUENCE: 2
uttttttutt ttttutttt tuttttttu                                29

<210> SEQ ID NO 3
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3 uttttttuttt ttutttttut ttttutt                                27

<210> SEQ ID NO 4
<211> LENGTH: 57
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<223> OTHER INFORMATION: 3'-amidated

<400> SEQUENCE: 4
uttttttutt ttttuttttt tuttttttut ttttuttttt ttutttttu ttttttt    57

<210> SEQ ID NO 5
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
gtgugtgugt gu                                                 12

<210> SEQ ID NO 6
<211> LENGTH: 50
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<223> OTHER INFORMATION: may be 3'-amidated or -biotin dU

<400> SEQUENCE: 6
acacacacac acacacacac acacacacac acacacacac acacacacac        50
```

<210> SEQ ID NO 7
<211> LENGTH: 15
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 7
tgcugctgcu gcugc                                                     15

<210> SEQ ID NO 8
<211> LENGTH: 63
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide
<220> FEATURE:
<223> OTHER INFORMATION: 3'-amidated

<400> SEQUENCE: 8
gcagcagcag cagcagcagc agcagcagca gcagcagcag cagcagcagc agcagcagca    60
gca                                                                  63

<210> SEQ ID NO 9
<211> LENGTH: 15
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 9
tcgucgtcgu cgucg                                                     15

<210> SEQ ID NO 10
<211> LENGTH: 63
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide
<220> FEATURE:
<223> OTHER INFORMATION: 3'-amidated

<400> SEQUENCE: 10
cgacgacgac gacgacgacg acgacgacga cgacgacgac gacgacgacg acgacgacga    60
cga                                                                  63

<210> SEQ ID NO 11
<211> LENGTH: 32
<212> TYPE: DNA
<213> ORGANISM: Artificial Sequence
<220> FEATURE:
<223> OTHER INFORMATION: Description of Combined DNA/RNA Molecule: Synthetic oligonucleotide

```
<220> FEATURE:
<223> OTHER INFORMATION: Description of Artificial Sequence: Synthetic
      oligonucleotide

<400> SEQUENCE: 11
gtgugtgugt gugtgutttu tttutttutt tu                                    32

<210> SEQ ID NO 12
<211> LENGTH: 61
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
uugtgtgtgt gtgugtgtgt gtgtgugtgt gtgtgtgugt gtgtgtgtgu gtgtgtgtgt     60
g                                                                      61

<210> SEQ ID NO 13
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
tgtgtgtgtg tgtgtgtgtg                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
acacacacac acacacacac                                                  20

<210> SEQ ID NO 15
<211> LENGTH: 61
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
ucacacacac acacacacac acacacacac acacacacac acacacacac acacacacac     60
a                                                                      61

<210> SEQ ID NO 16
<211> LENGTH: 20
<212> TYPE: DNA
```

```
-continued

<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
tgtgugtgtg tgtgugtgtg                                              20
```

MULTISIGNAL LABELING REAGENTS, AND PROCESSES AND USES THEREFOR

CROSS REFERENCE TO RELATED APPLICATIONS

This application is a divisional of U.S. patent application Ser. No. 10/407,818, filed Apr. 3, 2003 now U.S. Pat. No. 7,514,511.

FIELD OF THE INVENTION

This invention relates to compositions useful as multisignal labeling reagents. More particularly, these reagents are useful in a number of biochemical applications, including attaching signals to analyte-specific moieties, such as proteins and more specifically, antibodies. These reagents are also useful in labeling samples contemplated to be assayed in protein array systems. The addition of multiple signals in such reagents is useful in increasing detection sensitivity.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

The use of non-radioactive labels in biochemistry and molecular biology has grown exponentially in recent years. Among the various compounds used as non-radioactive labels, aromatic dyes that produce fluorescent or luminescent signal are especially useful. Notable examples of such compounds include fluorescein, rhodamine, coumarin and cyanine dyes such as Cy3 and Cy5. Composite dyes have also been synthesized by fusing two different dyes together (Lee et al., (1992) Nucl. Acids Res. 20; 2471-2488; Lee et al., U.S. Pat. No. 5,945,526 and Waggoner et al., in U.S. Pat. No. 6,008,373, all of which are hereby incorporated by reference).

Non-radioactive labeling methods were initially developed to attach signal-generating groups onto proteins. This was achieved by modifying labels with chemical groups such that they would be capable of reacting with the amine, thiol, and hydroxyl groups that are naturally present on proteins. Examples of reactive groups that were used for this purpose included activated esters such as N-hydroxysuccinimide esters, isothiocyanates and other compounds. Consequently, when it became desirable to label nucleotides and nucleic acids by non-radioactive means, methods were developed to convert nucleotides and polynucleotides into a form that made them functionally similar to proteins. For instance, U.S. Pat. No. 4,711,955 (incorporated by reference) disclosed the addition of amines to the 8-position of a purine, the 5-position of a pyrimidine and the 7-position of a deazapurine. The same methods that could add a label to the amine group of a protein could now be applied towards these modified nucleotides.

Labeled nucleotides have been used for the synthesis of DNA and RNA probes in many enzymatic methods including terminal transferase labeling, nick translation, random priming, reverse transcription, RNA transcription and primer extension. Labeled phosphoramidite versions of these nucleotides have also been used with automated synthesizers to prepare labeled oligonucleotides. The resulting labeled probes are widely used in such standard procedures as northern blotting, Southern blotting, in situ hybridization, RNAse protection assays, DNA sequencing reactions, DNA and RNA microarray analysis and chromosome painting.

There is an extensive literature on chemical modification of nucleic acids by means of which a signal moiety is directly or indirectly attached to a nucleic acid. Primary concerns of this art have been with regard to which site in a nucleic acid is used for attachment i.e. sugar, base or phosphate analogues and whether these sites are disruptive or non-disruptive (see for instance the disclosures of U.S. Pat. No. 4,711,955 and U.S. Pat. No. 5,241,060; both patents incorporated by reference), the chemistry at the site of attachment that allows linkage to a reactive group or signaling moiety a spacer group usually consisting of a single aromatic group (U.S. Pat. Nos. 4,952,685 and 5,013,831, both hereby incorporated by reference) or a carbon/carbon aliphatic chain to provide distance between the nucleic acid and a reactive group or signaling moiety and a reactive group at the end of the spacer such as an OH, NH, SH or some other group that can allow coupling to a signaling moiety and the nature of the signaling moiety.

More recently, U.S. patent application Ser. No. 10/096,075, filed on Mar. 12, 2002 (incorporated by reference) has disclosed novel labeling reagents that comprise a reactive group capable of creating a carbon-carbon bond between a marker or label and a desirable target molecule. This is in contrast to labeling reagents described previously, which employed protein derived chemistries involving formation of a bond between an amine, sulfhydryl or hydroxyl group and an appropriate reactive group. The presence and nature of the linker arm may also increase the biological or chemical activity of the labeled target molecule. Linker arms that may be used to provide appropriate spacing of signal groups in nucleic acids were also provided in this disclosure.

SUMMARY OF THE INVENTION

This invention relates to multisignal labeling reagents and their applications in the biochemical and related arts.

The present invention provides composition of matter comprising an oligomer or polymer comprising the following elements: a) two or more labeled moieties wherein the label or labels are chemically linked to the oligomer or polymer; b) one or more reactive groups; and c) one or more charged groups. Such charged groups (i) are covalently linked to the oligomer or polymer; or (ii) comprise part of the backbone of the oligomer or polymer; or (iii) any combination of the foregoing.

The present invention also provides a composition of matter comprising a nucleic acid strand or a complex of two or more nucleic acid strands wherein the strand or complex comprises (i) two or more labeled nucleotides or labeled nucleotide analogs, and (ii) one or more binding partners different from the labels.

Also provided by this invention is a composition of matter comprising a compound having the structure:

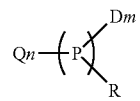

wherein Q represents a non-inherent charged group, n represents an integer of 1 or greater, D represents a label, m represents an integer equal to or greater than 2, R represents at least one reactive group and P represents an oligomer or polymer.

A further aspect of the present invention concerns a composition of matter comprising a compound having the structure:

In the structure above, D represents a label, m represents an integer equal to or greater than 2; R represents at least one reactive group and P represents a synthetic or chimeric oligomer or polymer. Also in the structure, D or at least one of the monomeric units of P comprises one or more charged groups.

Various processes are provided by this invention. In one particular aspect, the invention provides a process for labeling a target molecule that comprises attaching or binding a composition of matter to the target molecule. The composition comprises a nucleic acid strand or a complex of two or more nucleic acid strands wherein the strand or complex comprises (i) two or more labeled nucleotides or labeled nucleotide analogs, and (ii) one or more binding partners.

Additionally, the invention herein provides a composition prepared by a target labeling process comprising the steps of (a) providing: (i) a target for labeling; and (ii) a labeling reagent having the formula

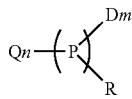

In the formula above, Q represents a non-inherent charged group, n represents an integer of 1 or greater, D represents a label, m represents an integer equal to or greater than 2, R represents at least one reactive group and P represents an oligomer or polymer; (b) reacting the target (i) and said labeling reagent (ii) to form the composition, the composition now having the formula

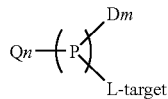

wherein L represents a linkage or linker between the oligomer or polymer and the target.

Another composition provided by this invention is prepared by a target labeling process comprising the steps of: (a) providing: (i) a target for labeling; and (ii) a labeling reagent having the formula

In the formula above D represents a label, m represents an integer equal to or greater than 2; R represents at least one reactive group, P represents a synthetic or chimeric oligomer or polymer, and D or at least one of the monomeric units of P comprises or represents one or more charged groups;

(b) reacting said target (i) and said labeling reagent (ii) to form said composition, said composition having the formula

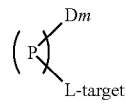

wherein L represents a linkage or linker between said oligomer or polymer and said target.

Numerous other aspects and embodiments of the present invention are described in further detail below.

BRIEF DESCRIPTION OF THE FIGURES

FIG. 1 shows various arrangements of single-stranded and double-stranded nucleic acid multisignal labeling reagents.

DETAILED DESCRIPTION OF THE INVENTION

The present invention discloses methods and compositions for making labeled targets, labeled analytes and labeled analyte specific moieties that can have increased sensitivity and solubility compared to previous art. Examples of analyte specific moieties that may find use with the present invention can include but not be limited to nucleic acids, proteins, antibodies, antigens, ligands, receptors, hormones and synthetic compounds. In one aspect of the present invention, novel labeling reagents are disclosed that comprise oligomers or polymers that comprise:

a) two or more labeled moieties where the label or labels are chemically linked to the oligomer or polymer
b) one or more reactive groups and
c) one or more charged groups that (i) are chemically linked to the oligomer or polymer or (ii) comprise part of the backbone of the oligomer or polymer or (iii) are any combination of the foregoing. When the novel labeling composition or reagent is used to label a compound for detection of a specific analyte, the oligomer or polymer should substantially lack a specific affinity for the analyte.

The multiple labeled groups should increase the amount of signal that is added to the analyte specific moiety; the presence of reactive groups will allow attachment of the multiple labeled groups to a desirable target and the presence of a charged group should allow maintenance or an increase of solubility. Examples of useful chemical linkages for joining labels or charged groups to the oligomer or polymer can include but not be limited to covalent bonds, non-covalent bonds, ionic bonds, ligands, receptors and complexes. Examples of labels or markers can include but not be limited to fluorescent compounds, phosphorescent compounds, chemiluminescent compounds, chelating compounds, electron dense compounds, magnetic compounds, intercalating compounds and energy transfer compounds. With reference to solubility, many fluorescent compounds used as labels have extensive aromatic or hydrophobic character and the charge group or groups of the present invention can provide compensation for this property. Examples of charged groups that may be useful in providing solubility can include but not be limited to phosphate, carboxylic, sulfone, amine and hydroxy groups. The charged groups can be an inherent part of the oligomer or polymer or they can be non-inherent modifications that are artificially introduced. Novel labeled analyte specific moieties may be used for the detection of any analyte including but not limited to nucleic acids, proteins, antibodies, antigens, ligands, receptors, hormones and drugs.

Each of the monomeric units of the oligomer or polymer can comprise a marker or the oligomer or polymer may comprise a mixture of labeled and unlabeled monomeric units. A labeled monomeric unit can comprise a single label or more than one label. When more than one label is included in a monomeric unit, they may be attached at the same site or at different sites on the monomer. An example of a monomeric unit with more than one label at a single site is a nucleotide that has a composite dye such as a fluorescein moiety linked to rhodamine moiety. On the other hand, the same methods used for making a composite dye described in U.S. patent application Ser. No. 10/096,076, filed on Mar. 12, 2002, incorporated herein by reference, could be applied to the synthesis of tandem dimers, trimers etc. of the same dye. As such, the user is able to direct the number of monomeric units, the proportion of labeled monomeric units, and the number of labels per monomer.

Examples of monomeric units that can be used to create an oligomeric or polymeric labeling reagent can include but not be limited to amino acids, nucleotides, carbohydrates, sugars, aromatic compounds and any organic compound that may be derivatized to be able to form oligomeric or polymeric moieties. Modified versions or analogues of any monomeric units may also be used. Examples of analogues that might find use in the present invention can comprise but not be limited to nucleotide analogues comprising universal or degenerate bases (Reviewed in Lockahart 2001, Nucl Acids Res 29; 2437-2447), peptide nucleic acid monomers (Nielsen et al., 1991 Science 254; 1497), non-nucleotide spacer groups (U.S. Pat. No. 5,696,251), sugar analogues (Ono et al., 1997 Nucl Acids Res 25; 4581-4588), methylphosphonamidites (Loschner and Engels 1988 Nucleosides Nucleotides 7; 729) and phosphorothioates (Stec et al., 1984 J. Am. Chem. Soc. 106; 6077) all of which are incorporated by reference.

Examples of oligomers or polymers made from such monomeric units can include but not be limited to nucleic acids, abasic nucleic acids, peptide nucleic acids, polypeptides, proteins, oligosaccharides, polysaccharides and organic polymers. The oligomers or polymers used in the present invention may be isolated from biological sources or they may be created synthetically or in vitro. It may be desirable that the labels and/or reactive groups that are chemically linked to the oligomers or polymers are not intrinsic to such oligomers and polymers. The oligomers or polymers may be homopolymeric and comprise multiples of only one particular type of monomeric unit or they may be heteropolymeric or chimeric and comprise different monomeric units. For example, a chimeric oligomer or polymer can be a nucleic acid construct that comprises both a normal nucleic acid segment and a peptide nucleic acid segment, a combination of nucleotides and amino acids or a combination of a segment of an abasic nucleic acid and a segment comprising a peptide nucleic acid. The present invention finds especial use when the labeling reagent of the present invention is used to label an oligomeric or polymeric target molecule, where the monomeric units of the labeling reagent may have a different nature from the monomeric units of the olgomeric or polymeric target. As an example of this, the oligomeric or polymeric moieties can be nucleic acid constructs that comprise labeled nucleotides or nucleotide analogues and at least one reactive group thereby providing the ability to attach multiple labels to one or more of the amino acids that make up a target protein. Any of the markers, linkers and reactive groups that had been disclosed previously in the literature may find use in this particular embodiment of the present invention.

Additionally, even when the monomeric units of an oligomer or polymer may be of a similar nature, they may be the same or they may be different. For instance a nucleic acid polymer may be a homopolymer comprising a reiteration of a single base or it can be a heteropolymer having varied nucleotides. A polypeptide may be hompopolymeric and comprise multiples of a single amino acid or it may be heteropolymeric and comprise different amino acids. The labels in an oligomeric or polymeric labeling reagent may also be the same or they may be different. For instance, a labeling reagent that comprises two different dyes attached at discrete intervals on a polynucleotide may participate in energy transfer for signal generation.

Oligomers or polymers of the present invention may comprise a single chain structure linking the monomeric units together or they may comprise more than one chain. For example, branched, double-stranded and triple-stranded nucleic acids may all find use with present invention. Such multi-chain structures may provide useful properties. For example, a double-stranded nucleic acid is more rigid than a single stranded nucleic acid. The use of a double-stranded structure may allow better control over the distribution or spacing of labeled moieties where proximity or lack of proximity may be desirable. For instance, efficient signal generation by means of energy transfer depends upon a close proximity of donor and acceptor moieties and as such, establishment of a proximity between these moieties can be beneficial. On the other hand, if a single dye species is being used as signal generators, a close proximity of some dye molecules can lead to a self-quenching phenomenon and spreading out the locations of the dyes could be beneficial. The use of more than one chain may also convey other useful properties such as increasing the amount of signal generated or increasing the charge number. Multiple chains may also endow the system with flexibility of use. For example, a first nucleic acid strand may comprise a reactive group and a second nucleic acid strand with complementary sequences can comprise signal groups. By complementary base pairing between these strands, a complex can be formed that comprises a reactive group and signaling groups. To illustrate these points further, some variations on the use of multiple chains are shown in FIG. 1. The use of multiple chains for the novel labeling reagent of the present invention can be extended further in preparation of reagents or labeled moieties that can be used in parallel. For instance, a first chain comprising a reactive group can be mixed with either of two second chains to prepare two different compounds that use the same reactive group but comprised different labels from each other. The oligomers and polymers of the present invention may also comprise non-polymeric components as well. For example, they may comprise termini or extended chains with extended multiple charged groups. Other groups that may offer useful additional properties may also find use with the present invention.

Previous art has disclosed the use of nucleic acids as labeling agents for proteins (U.S. patent application Ser. No. 08/479,995, filed on Jun. 7, 1995, published/granted by the European Patent Office as European Patent No. 0 128 332 B1). However, the methods in that reference described the attachment of an unlabeled polynucleotide to targets followed by hybridization of labeled complementary nucleic acids. In contrast, in the present invention, when a complex comprising two or more oligonucleotides or polynucleotides is used to convey multiple signals, a preformed reagent is used that comprise the signals as well as one or more reactive groups. In this way, the target doesn't proceed through a hybridization reaction. The methodology also allows purification of the complex prior to attachment to a target insuring that there is maximal amount of labeled nucleic strands in the complexes with reactive groups. Due to an interest in labeling nucleic acids, a wide variety of techniques are known in the art for joining nucleic acids to non-nucleic acids. Examples of such methods are disclosed in Jablonski et al., 1986 Nucl acids Res 14; 6115-6128, U.S. patent application Ser. No. 08/479,995 (filed Jun. 7, 1995), U.S. patent application Ser. No. 09/896,897 (filed Jun. 30, 2001) and "Methods for Nonradioactive Labeling of Nucleic Acids" by Christopher Kessler pp 42-109 in *Nonisotopic Probing, Blotting and Sequencing*, $2^{nd}$ edition, Larry J. Kricka (Ed.), 1995, Academic Press, Inc., San Diego, Calif., all of which are hereby incorporated by reference.

It is a further aspect of the present invention that when the oligomer or polymer is a nucleic acid, the reactive group may be replaced by a binding partner. Thus, the interaction of a binding partner in the labeling reagent with its binding partner counterpart on the target molecule will allow attachment of the labels to the target molecule. Examples of binding partner pairs can include but not be limited to ligand/receptor, hormone/receptor, biotin/avidin, biotin/strepavidin and antigen/antibody pairs.

As such, in this aspect of the present invention, a novel labeling reagent is disclosed that comprises a nucleic acid strand or a complex of nucleic acid strands which further comprises two or more labels and one or more binding partners where the binding partners may be different from the labels or they may be the same. This aspect of the present invention finds especial use where the labeled nucleic acid strand or complex is linked to a non-nucleic acid target by means of a binding partner. Thus although previous art has described the ability to label nucleic acids by binding labeled proteins, this aspect of the present invention discloses the ability to label proteins by binding labeled nucleic acids.

In a further aspect of the present invention, the novel or oligomeric or polymeric units comprise one or more reactive groups R which may be connected by linker arm L which is a chain of atoms of any length that may be comprised of carbon, nitrogen, oxygen, sulfur in any combination and any other possible atom. The connecting chain can be saturated, unsaturated or can contain aromatic rings and the linking chain can be flexible or rigid. The connecting chain can further comprise any of the rigid units previously disclosed in U.S. patent application Ser. No. 10/096,075 (filed Mar. 12, 2002) incorporated herein by reference. In this aspect of the invention, examples of reactive groups can include but not be limited to active esters, groups capable of forming a carbon-carbon bonds and groups capable of forming bonds with O, N or S. Examples of such groups can include but not be limited to isothiocyanate, isocyanate, monochlorotriazine, dichlorotriazine, mono- or di-halogen substituted pyridine, mono- or di-halogen substituted diazine, maleimide, aziridine, sulfonyl halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal, aldehyde, carbon-carbon double bonds, mercury salts, and any group capable of reacting with carbon-carbon double bonds, amines, hydroxyl groups, sulfhydryl groups and halogens. The reactive groups may also participate in formation of a coordinate bond when R comprises a ligand or a metal. A reactive group R can be attached to the oligomeric or polymeric moiety through a linker arm L as described above or if desired it may be attached directly without the use of a linker arm. It is a further aspect of this invention that the reactive group can be chemically linked to the novel labeling reagent at a terminus, a side chain or an internal site of the oligomeric or polymeric moiety. Furthermore, the novel polymeric composition described may also contain additional alkyl, aryl and/or polar or charged groups on the backbone, linking arm or the dyes or labels. The polar or charged groups may include but are not limited to halogen, substituted or unsubstituted alkyl or aryl groups, saturated or unsaturated alkyl groups, alkoxy, phenoxy, amino, amido, and carboxyl groups, polar groups such as nitrates, sulfonates, sulfhydryl groups, nitrites, carboxylic acids, phosphates or any other such group or substitutent.

In another aspect of the present invention, the novel oligomeric or polymeric labeling reagents can be described as follows:

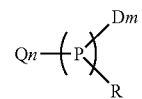

In the diagram above, Q refers to a charged group and n is equal to an integer of 1 or greater; D refers to a dye or other suitable label and m is equal to or greater than 2; R refers to at least one reactive group that may be used to join the labeling reagent to a suitable target and P represents the oligomer or polymer. The charged groups and dyes may be attached to each of the monomeric units that comprise P or only some of the monomeric units may comprise these groups.

In another aspect of the present invention, the novel oligomeric or polymeric labeling reagents can be described as follows:

In the diagram above, D refers to a dye or other suitable label and m is equal to or greater than 2; R refers to at least one reactive group; P represents the oligomer or polymer and where D or one of the monomeric units of P comprises one or more charged groups. The dyes may be attached to each of the monomeric units that comprise P or only some of the monomeric units may comprise these groups.

In another aspect of the present invention, novel compositions of the form shown below are disclosed where the novel oligomeric or polymeric labeling reagents of the present invention have been used to label suitable target molecules.

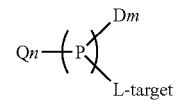

In the diagram above, Q refers to a charged group and n is equal to an integer of 1 or greater; D refers to a dye or other suitable label and m is equal to or greater than 2; P represents an oligomer or polymer; and L is the linkage that joins the labeling reagent to the target molecule. The charged groups and dyes may be attached to each of the monomeric units that comprise P or only some of the monomeric units may comprise these groups. L may comprise any of the linkage arms described previously or it may comprise the linkage formed between a reactive group R and the appropriate chemical group on the target molecule. The target can be chosen from a group that includes but is not limited to peptides, proteins, antibodies, enzymes, enzyme substrates, ligands, hormones, receptors, antigens, haptens, lectins, avidin, streptavidin, toxins, carbohydrates, oligosaccharides, polysaccharides, ribonucleotides, deoxyribonucleotides, dideoxyribonucleotides, analogues of deoxynucleotides, ribonucleotides and dideoxynucleotides, modified deoxynucleotides, modified ribonucleotides, modified dideoxynucleotides oligonucleotides, polynucleotides, and any other analyte specific moiety that can form a linkage with the reactive group R.

In another aspect of the present invention, novel compositions of the form shown below are disclosed where the novel oligomeric or polymeric labeling reagents of the present invention have been used to label suitable target molecules:

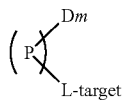

In the diagram above, D refers to a dye or other suitable label and m is equal to or greater than 2; P represents an oligomer or polymer; L is the linkage that joins the labeling reagent to the target molecule and where D or one of the monomeric units of P comprises one or more charged groups. The dyes may be attached to each of the monomeric units that comprise P or only some of the monomeric units may comprise these groups. L may comprise any of the linkage arms described previously or it may comprise the linkage formed between a reactive group R and the appropriate chemical group on the target molecule. The target may be chosen from any members of the group described previously.

The various aspects of the present invention that provide multiple signals allow the synthesis of highly sensitive labeling compositions. In methods previously used for preparing labeled reagents such as enzymatic incorporation, the number of dye units is often limited because of poor incorporation of the dye by the enzyme. Furthermore, it is also possible for two or more dye units to be placed adjacent to each other after enzymatic incorporation, which often results in the quenching of the signal. One advantage of the present invention is that the placement of the dyes can be specifically controlled so that the required number of dye units and spacing between them can be designed for optimal signal. This can result in labeling reagents with labeled units that produce the maximum amount of signal with minimal quenching from adjacent units. The novel labeling reagents of the present invention can be used for a wide variety of purposes where increased signal strength is beneficial.

It is a further aim of the present invention to provide unlabeled reagents that can be used in conjunction with the present invention or with other labeling reagents or labeled materials. For instance, when a compound comprises a target specific moiety and a label, the highest level of signal to noise (S/N) is achieved when binding takes place through the agency of the target specific moiety and not through the label itself, or any components used to join the label to the target specific moiety. By definition, any part of the compound that is not target specific is incapable of discrimination and binding of such moieties to non-target molecules could potentially lead to a rise in background signal generation and a subsequent lowering of the S/N ratio. Therefore, the present invention discloses that unlabeled oligomeric and polymeric compounds that are similar to labeled oligomeric or polymeric moieties used to label target specific moieties can be used in assays detecting the presence or quantity of a particular analyte where the unlabeled oliogmers or polymers can suppress non-specific binding by the oligomers or polymeric components of labeled compounds.

As an illustrative example of this method, an antibody labeled with an oligonucleotide comprising multiple fluorescein moieties is used as a detection reagent. Unlabeled oligonucleotides can be used to block nonspecific binding by such a reagent. The blocking reagent can be used either prior to or during exposure of the specimen to the antibody detection reagent. The nucleic acid can be a heterogeneous collection of sequences. For instance, salmon sperm or calf thymus DNA has commonly been used in assays with labeled DNA probes to eliminate non-specific general binding of nucleic acids. Conversely, the sequence of the nucleic aid used to label the antibody could also be used for a blocking reagent, i.e a discrete sequence. It is also understood that combinations or mixtures of discrete, random, permutational or heterogeneous nucleic aids may be used for this purpose.

The following examples are offered by way of illustration and not by way of limitation to the present invention.

DESCRIPTION OF THE PREFERRED EMBODIMENTS

The examples in this application are listed below:
Example 1 Multisignal Reagent with reactive group at 5' end
Example 2 Use of Multisignal Reagent with SH groups on proteins
Example 3 Modification of proteins for use with Multisignal Reagent
Example 4 Addition of bromoacetyl group to the 5' end of Multisignal Reagent
Example 5 Multisignal labeling reagent used with glycoprotein
Example 6 Multisignal Reagent with reactive group at 3' end
Example 7 Synthesis of Multisignal Reagent by TdT
Example 8 Synthesis of Multisignal Labeling reagent using mercuration
Example 9 Double-stranded Multisignal Reagent
Example 10 Multisignal Reagents used for protein array
Example 11 Multisignal Reagent with tailed Signal Reagents
Example 12 Antibody labeled with Double-stranded Multisignal Reagent using Biotin
Example 13 Single-stranded Multisignal Reagent using Biotin and Noise Suppressor used for microarray chip
Example 14 Multisignal Reagent used for microarray chip using complementary nucleic acid
Example 15 Multisignal Reagent for microarray chip using energy transfer Example 1

Multisignal Labeling Reagent a) a 33-mer oligonucleotide with the following structure is synthesized:

(SEQ ID NO: 1)
5' PO$_4$- T TU* T T T TT U* T T T T T U* T T T T TU*

T T T T T U* T T T T T U* - 3' where the 5' end has a phosphate group and the oligonucleotide comprises allylamine modified Uridine moieties (symbolized as U*)

b) The active ester of the aphenylic Texas Red analogue described by Stavrianopoulos in U.S. patent application Ser. No. 10,096,075, filed on Mar. 12, 2002, can be reacted with the allylamine moieties in the oligonucleotide to produce a labeled oligonucleotide using the same procedures described in that reference for attachment of the aphenylic Texas Red analogue to allylamine modified dUTP.

c) The 5' phosphate of the labeled oligonucleotide is reacted with a primary dialkylamine by the procedure described by Halloran and Parker (1966, J. Immunol. 96; 373) thereby transforming the labeled oligonucleotide into an multisignal labeling reagent with a 5' amine group.

d) The primary amine at the 5' end is then reacted with a 20 fold molar excess of succinylmaleic acid active ester at pH 7.8 for 45 minutes at room temperature to tether the maleimide group to the 5' end. The pH is immediately adjusted to pH 4-5 by adding concentrated acetic acid and the maleimide derivatized oligonucleotide is precipitated by ethanol. It is then resuspended in LiAc (pH 4) buffer and precipitated again. Before use, the maleimide derivatized oligonucleotide is dissolved in Acetate buffer (pH 5.5). This procedure generates a multisignal labeling reagent that comprises 6 Texas Red dye moieties and a single reactive group for attachment to a desirable target.

Example 2

Use of Multisignal Labeling Reagent with Proteins

The reagent from Example 1 can be used directly to label a protein that has available syulfhydryl groups. For instance, BSA can be labeled at room temperature by reacting it with the maleimide derivatized reagent at pH 5.5.

Example 3

Modification of Proteins for Use with Multisignal Labeling Reagent

Proteins that lack available sulfhydryl groups may also be used with the reagent from Example 1. For instance, an antibody can be treated with N-acetyl-homocysteine thiolactone at pH 9 thereby introducing sulfhydryl groups that can be labeled with the maleimide derivatized reagent as described above in Example 2. By varying the reaction time and concentration of the N-acetyl-homocysteine thiolactone, the number of sulfhydryl groups introduced into a protein can be controlled. To retain biological activity, it is preferred that an antibody be modified with at most 2-3 sulfhydryl groups.

Example 4

Modification of Multisignal Labeling Reagent

The multisignal labeling reagent described in step c) of Example 1 is treated with bromoacetic acid NHS ester to tether a bromoacetyl group to the 5' end. This group is very reactionary to primary amines and can be used at pH 9 to label a protein or other desirable group that contains primary amines or thiol groups. As described previously, these groups can be native to the target molecule or introduced.

Example 5

Multisignal Labeling Reagent Used with Glycoprotein

In addition to the amine and sulfhydryl groups described previously, many proteins that are isolated from mammalian cells are gycosylated, thereby providing an additional target group that can be used for attachment. A notable example of such proteins are antibodies. Oxidation of IgG can be carried out in the dark at 4° C. for 20 minutes with 10 mM periodate at pH 4-5 to introduce aldehyde groups into the antibody. The excess periodate is removed afterwards by G50 fractionation. A modification reagent is prepared by reacting cystathione with Elman's Reagent thus blocking the thiol moiety with a removable group. The aldehyde groups on the glycon portion of the antibody are then reacted with a 40 fold excess of the modification reagent at pH 6 for one hour at room temperature. The pH is then raised to pH 9, the solution is cooled and the Schiff's base is reduced with $NaBH_4$. This reduces the Schiff's base to an amine and liberates the thiol. The excess $NaBH_4$ is destroyed by adding acetate buffer (pH 4). The thiol labeled IgG is now available for linkage with the either the maleimide dervatized reagent from Example 1 or the bromoacetyl modified reagent from Example 4. It should be noted that this method results in a very controlled extent of labeling since it only takes place on sites where glycosylation has taken place. For example, the antibody used in this example is glycosylated in the constant region. As such, attachment of the labeling reagent should not interfere with the variable region, the part of the antibody that is responsible for the binding of the antibody to its antigen target.

Example 6

Multisignal Reagent with a Reactive Group at the 3' End

A 29-mer oligonucleotide with the following structure is synthesized;

(SEQ ID NO: 2)
5' -$U^F$ T T T T T T $U^F$ T T T T T T $U^F$ T T T T T T $U^F$ T T T T T T $U^F$ - $NH_2$ 3' where the oligonucleotide comprises a 3' primary amine and Uridines that have fluorescein labels (symbolized by $U^F$). Phosphoramidites and CPG for making an oligonucleotide with these modification are commercially available. Alternatively, a phosphoramidite for synthesis of an oligonucleotide with a primary amine in the 5' end could have been used to synthesize a similar labeled oligonucleotide. This product comprises 5 fluorescein moieties and a single amine group. This reagent may be used with the same processes described previously for Examples 1, 2, 3, 4 and 5.

Example 7

Use of Terminal Transferase to Synthesize a Multisignal Labeling Reagent a) A 27-mer oligonucleotide with the following structure is synthesized;

(SEQ ID NO: 3)
5' - U* T T T T T U* T T T T T U* T T T T T U* T T

T T T U*T T - 3' where the oligonucleotide comprises allylamine modified Uridines (symbolized by U*). Attachment of the active ester of Alexa Fluor 555 (Molecular Probes, Inc, Eugene, Oreg.) can be carried out by the methods previously described in Example 1.

b) The labeled oligonucleotide can be further reacted by the addition of a dideoxy version of allylamine dUTP by Terminal Transferase. This step will introduce a single amine group into the 3' end of the oligonucleotide, thereby creating a labeling regent with 5 Alexa dyes and a single amine group. This labeling reagent can then be used as described previously.

Example 8

Synthesis of Multisignal Labeling Reagent Using Mercuration

A 57-mer oligonucleotide with the following structure is synthesized:

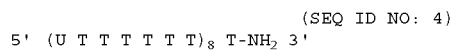

5' (U T T T T T T)$_8$ T-NH$_2$ 3' (SEQ ID NO: 4)

where the 3' end has an amine group. The oligonucleotide is treated with a 3 fold molar access of Mercuric Acetate in acetate buffer (ph 4.0) for 5 hours at 65° C. to mercurate the 5 position of the uridine ring of the oligonucleotides. The mercurated oligonucleotides are then precipitated with ethanol and kept at −20° C. until needed. The oligonucleotide is then reacted with a Cy dye that comprises a terminal double bond reactive group as described by Stavrianopoulos et al, in U.S. patent application Ser. No. 10,096,075 filed Mar. 12, 2002, hereby incorporated by reference. The resultant oligonucleotide should then comprise a single amine reactive group at the 3' end and a Cy dye at each of the 8 sites where there was a U. This labeling reagent may then be used as described above.

Example 9

Protein Labeled by Means of Two Strands of Nucleic Acid a) A 12-mer oligonucleotide with the following structure is synthesized;

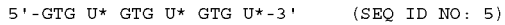

5'-GTG U* GTG U* GTG U*-3' (SEQ ID NO: 5)

where the oligonucleotide comprises allylamine modified Uridines (symbolized by U*).

b) The active ester of the aphenylic Texas Red analogue used in Example 1 can be reacted with the allylamine moieties in the oligonucleotide to produce a Signal Oligonucleotide using the same procedures described above.

c) A 50-mer Attachment Oligonucleotide with the following structure is synthesized;

5'-(A C)$_{25}$-NH$_2$ 3' (SEQ ID NO: 6)

d) The Texas Red labeled Signal Oligonucleotide is annealed to the Attachment Oligonucleotide to form a Multisignal Labeling Reagent. Due to the redundancy of the dinucleotide repeats, hybridization should enjoy fast kinetics. The Signal Oligonucleotides are smaller than the Attachment Oligonucleotide such that there is sufficient room for as many as 4 Signal Oligonucleotides to bind to each Attachment Oligonucleotide of the Multisignal Labeling Reagent. This would result in 12 signal moieties potentially being attached to every site on a target that is linked through the amine group of the Multisignal Labeling Reagent. Using the 2° C. per A/T base-pair and 4° C. per G/C base-pair rule, the theoretical Tm of the Signal Oligonucleotides should be about 36° C. As such, the Multisignal Labeling Reagent complexes should be quite stable at Room Temperature. Even higher Tm's will probably be realized since hybridization of two Signal Oligonucleotides on adjacent sites of the Attachment Oligonucleotide should allow stacking interactions that will favor the thermal stability of each oligonucleotide.

e) The Multisignal Labeling Reagent can be attached to a protein through the amine group as described previously to form a labeled protein comprising multiple signals at each attachment site on the protein.

Example 10

Preparation of Samples for a Protein Array a) A 15-mer oligonucleotide with the following structure is synthesized;

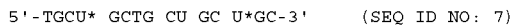

5'-TGCU* GCTG CU GC U*GC-3' (SEQ ID NO: 7)

where the oligonucleotide comprises allylamine modified Uridines (symbolized by U*)

b) The active ester of the aphenylic Texas Red analogue is reacted with the allylamine moieties in the oligonucleotide to produce Signal Oligonucleotide #1 by the methods described previously in Example 1. The Tm of this oligonucleotide should be about 50° C.

c) Attachment Oligonucleotide #1 (a 63-mer) with the following structure is synthesized;

5'-(GCA)$_{21}$-NH$_2$ 3' (SEQ ID NO: 8)

d) Signal Oligonucleotide #1 is annealed to Attachment Oligonucleotide #2 to form Multisignal Labeling Reagent #1 which at saturation values should have 8 Texas Red moieties bound per 3' NH$_2$ group.

e) A 15-mer oligonucleotide with the following structure is synthesized;

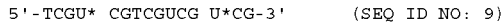

5'-TCGU* CGTCGUCG U*CG-3' (SEQ ID NO: 9)

where the oligonucleotide comprises allylamine modified Uridines (symbolized by U*).

f) Using the same methods as in step (b), the active ester of Alexa Fluor 647 (Molecular Probes, Inc, Eugene, Oreg.) is reacted with the allylamine moieties in the oligonucleotide to produce Multisignal Oligonucleotide #2. The Tm of this oligonucleotide should also be about 50° C.

g) Attachment Oligonucleotide #2 (a 63-mer) with the following structure is synthesized;

5'-(CGA)$_{21}$-NH$_2$ 3' (SEQ ID NO: 10)

h) Signal Oligonucleotide #2 is annealed to Attachment Oligonucleotide #2 to form Multisignal Labeling Reagent #2 which at saturation values should have 8 Alexa moieties bound per 3' NH$_2$ group.

i) Protein sample #1 is reacted with Multisignal Labeling Reagent #1 from step (d) and Protein sample #2 is reacted with Multisignal Labeling Reagent #2 from step (d) using any of the methods described in the previous examples.

These samples are now ready to be applied to a protein array where signals from protein sample #1 (Texas Red) will be distinguishable from signals from Protein sample #2 (Alexa). As described above, linkage of a Multisignal Labeling Reagent of this Example of the present invention should allow joining as many as 8× the amount of signal moieties as would result from using a single dye with an amino group.

Example 11

Multisignal Labeling Reagent with Single-Stranded Tails a) A 50-mer Attachment Oligonucleotide with the following structure is synthesized;

```
5'-(A C)25-NH2 3'         (SEQ ID NO: 6)
``` b) A 32-mer Signal Oligonucleotide with the following structure is synthesized;

```
                                   (SEQ ID NO: 11)
5'-GTG U* GTG U* GTG U* GTG U* T T T U* T T T U* T
T T U* T T T U*-3'
``` where the oligonucleotide comprises allylamine modified Uridines (symbolized by U*)

c) The active ester of the aphenylic Texas Red analogue is reacted with the allylamine moieties in the oligonucleotide to produce a tailed Signal Oligonucleotide. The 16 base segment at the 5' end of the Signal Oligonucleotide is complementary to the Attachment Oligonucleotide of step (a) and should have a Tm of about 48° C. based on 8 G's and 8 T/U's. The 16 base 3' tail segment of the Signal Oligonucleotide consisting of T's and U*'s should contribute signal but should not participate in binding to the Attachment Oligonucleotide.

d) Hybridization of the Signal Oligonucleotides to the Attachment Oligonucleotide will form a Multisignal Labeling Reagent that could provide as many as three Signal Oligonucleotides, each having 8 signal moieties, for a net total of 24 signal moieties potentially bound to each site where the Attachment Oligonucleotide portion of the Multisignal Reagent will be linked to the protein target.

The unlabeled Attachment Oligonucleotide portion of the Multisignal Reagent is used for linkage to a protein through the amine group as described previously to form a labeled target comprising one or more Multisignal Labeling Reagents.

Example 12

Double-Stranded Multisignal Labeling Reagent with Biotin as a Binding Partner a) A 50-mer Biotinylated Attachment Oligonucleotide with the following structure is synthesized;

```
5'-(A C)25-biotin dU 3'       (SEQ ID NO: 6)
```

Phosphoramidites for a 3' biotin labeled nucleotide are readily available from numerous commercial sources.

b) The tailed Signal Oligonucleotides from step (c) of Example 9 are hybridized to the Biotinylated Attachment Oligonucleotide to form a Biotinylated Multisignal Labeling Reagent. As described previously, this complex could comprise as many as 24 signal moieties with only a single biotin attachment moiety.

c) Biotinylated Antibodies are readily available from a number of commercial sources. A Biotinylated Antibody can be can be bound to appropriate target antigens in a tissue section specimen and amplified detection of the presence of antigens can be carried out by first binding strepavidin followed by signal generation through binding of the Biotinylated Multisignal Labeling Reagent from step (b).

Example 13

Single-Stranded Multisignal Reagent with Biotin as a Binding Partner and Addition of Noise Suppressor a) a 61-mer oligonucleotide with the following structure is synthesized:

```
                                        (SEQ ID NO: 12)
5' Biotin U-(U* G T G T G T G T G T G)5-3'
``` where the 5' end has a biotinylated U and the oligonucleotide comprises allylamine modified Uridine moieties (symbolized as U*)

b) The active ester of Cy 3 dye (Amersham Biosciences, Piscataway, N.J.) can be reacted with the allylamine moieties in the oligonucleotide using the same procedures described above. To form a Cy3 labeled Biotinylated Multisignal Reagent:

c) a 20-mer oligonucleotide with the following sequence is synthesized:

```
5'-(TG)10-3'             (SEQ ID NO: 13)
``` without labels or biotin to provide a Noise Suppressor.

d) Poly A mRNA is amplified according to the procedure described in Rabbani et al., in U.S. application Ser. No. 09/896,897, filed on Jun. 30, 2001 (incorporated by reference) where biotin is incorporated during in vitro transcription of the double-stranded cDNA collection to produce labeled anti-sense RNA.

e) The biotinylated RNA is fragmented and hybridized to a High Density microarray chip form Affymetrix according to the manufacturer's instructions (Affymetrix, Inc. Santa Clara, Calif.).

e) The chips are incubated with Strepavidin according to the Affymetrix instructions.

f) Instead of using biotinylated phycoerythrin as described in the Affymetrix instructions, the chip is incubated with a mixture of the Cy3 labeled Biotinylated Multisignal Reagent from step (b) and the Noise Suppressor from step (c).

g) After appropriate washing, signal generation from each locus is then measured.

Example 14

Single-Stranded Multisignal Labeling Reagent with Biotin as a Binding Partner and Addition of Unlabeled Complement a) a 61-mer oligonucleotide with the following structure is synthesized:

```
                                        (SEQ ID NO: 12)
5' Biotin U-(U* G T G T G T G T G T G)5-3'
``` where the 5' end has a biotinylated U and the oligonucleotide comprises allylamine modified Uridine moieties (symbolized as U*).

b) The active ester of Cy 3 dye (Amersham Biosciences, Piscataway, N.J.) can be reacted with the allylamine moieties in the oligonucleotide using the same procedures described above. To form a Cy3 labeled Biotinylated Multisignal Labeling Reagent.

c) A 20-mer oligonucleotide with the following structure is synthesized:

$$5'-(AC)_{10}-3' \quad \text{(SEQ ID NO: 14)}$$

without labels or biotin to provide a Multisignal Reagent Complement. The Tm of this oligonucleotide should be about 60° C. based on 10 C's and 10 A's.

d) Poly A mRNA is amplified according to the procedure described in ENZ 61 where biotin is incorporated during in vitro transcription of the double-stranded cDNA collection to produce labeled anti-sense RNA.

e) The biotinylated RNA is fragmented and hybridized to a High Density microarray chip from Affymetrix according to the manufacturer's instructions (Affymetrix, Inc., Santa Clara, Calif.).

e) The chips are incubated with Strepavidin according to the Affymetrix instructions.

f) Instead of using biotinylated phycoerythrin as described in the Affymetrix instructions, the chip is incubated with a mixture of the Cy3 labeled Biotinylated Multisignal Reagent from step (b) and the Multisignal Reagent Complement from step (c). Hybridization of the Multisignal Reagent Complement to the Cy3 labeled Biotinylated Multisignal Reagent can take place during this step or if desired they can be preinubated together pripor to application to the chip. By endowing the Cy3 labeled Biotinylated Multisignal Reagent with double-stranded character, quenching caused by interactions of the Cy 3 moities could be reduced. Also if desired, the Noise Suppressor from step (c) of Example 11 may be included.

g) After appropriate washing, signal generation from each locus is then measured.

Example 15

Multisignal Labeling Reagent with Biotin and Energy Transfer a) a 61-mer oligonucleotide with the following structure is synthesized:

$$\text{(SEQ ID NO: 15)}$$
$$5'\text{ Biotin U-}(C^F \text{ A C A C A C A C A C A})_5\text{-3'}$$

where the 5' end has a biotinylated U and the oligonucleotide comprises fluoroscein modified Cytidine moieties (symbolized as CF) to form an Energy Donor Multisignal Labeling Reagent.

b) a 20-mer oligonucleotide with the following structure is synthesized:

$$\text{(SEQ ID NO: 16)}$$
$$5'\text{-T G T G U* G T G T G T G U* G T G T G-3'}$$

where the 5' end has a biotinylated U and the oligonucleotide comprises allylamine modified Uridine moieties (symbolized as U*). The Tm of this oligonucleotide should be about 60° C. based on 10 G's and 10 T/U's.

c) The active ester of aphenylic Texas Red can be reacted with the allylamine moieties in the oligonucleotide using the same procedures described above to form an Energy Acceptor Multisignal Labeling Reagent.

d) The Energy Donor Multisignal Reagent from step (a) and the Energy Acceptor Multisignal Labeling Reagent from step (c) are hybridized together to form an Energy Transfer Multisignal Labeling Reagent which comprises a single biotin and as many as 5 donors and 6 acceptors.

e) The Energy Transfer Multisignal Labeling Reagent can then be used as described above.

Many obvious variations will no doubt be suggested to those of ordinary skill in the art in light of the above detailed description and examples of the present invention. All such variations are fully embraced by the scope and spirit of the invention as more particularly defined in the claims that now follow.

What is claimed is:

1. A composition of matter comprising a nucleic acid strand or a complex of two or more nucleic acid strands wherein said strand or complex comprises (i) two or more labeled nucleotides or labeled nucleotide analogs, and (ii) one or more binding partners different from said labels, wherein said binding partner is attached to said strand or said complex through a linker.

2. The composition of claim 1, wherein said strand or complex comprises one or more unlabeled nucleotide analogs.

3. The composition of claim 1 or 2, wherein said nucleotide analogs are selected from the group consisting of abasic nucleotides, spacer groups and peptide nucleic acid subunits.

4. The composition of claim 1, wherein said labels are selected from the group consisting of fluorescent compounds, phosphorescent compounds, chemiluminescent compounds, chelating compounds, electron dense compounds, magnetic compounds, intercalating compounds, energy transfer compounds, and any combination thereof.

5. The composition of claim 1, wherein said binding partners are selected from the group consisting of ligand/receptor, hormone/receptor, biotin/avidin, biotin/streptavidin and antigen/antibody pairs.

6. The composition of claim 1, wherein said linker is attached to said strand or complex on a nucleotide or nucleotide analog and said attachment is through the sugar or phosphate position of said nucleotide or nucleotide analog.

7. The composition of claim 1, wherein said linker comprises one or more carbon, nitrogen, oxygen, phosphorus or sulfur atoms, or a combination thereof.

8. The composition of claim 1, wherein said linker comprises one or more peptide bonds, alkyl chains, alkene groups, alkyl groups, aryl groups, conjugated systems, sugars or derivatives thereof.

9. The composition of claim 1, wherein said nucleic acid strands are linear.

10. The composition of claim 1, wherein said composition comprises a nucleic acid complex that is formed through base-pairing.

11. The composition of claim 1, wherein said linker is attached to said strand or complex on a nucleotide or nucleotide analog and said attachment is through a sugar or an analog thereof.

12. The composition of claim 1, wherein said linker is attached to said strand or complex on a nucleotide or nucleotide analog and said attachment is through a phosphate or an analog thereof.

13. The composition of claim 1, wherein said nucleic acid strands are branched.

14. The composition of claim 1, wherein said composition comprises a nucleic acid complex that is formed through triple strand formation.

* * * * *